United States Patent [19]
Puno et al.

[11] Patent Number: 5,360,431
[45] Date of Patent: Nov. 1, 1994

[54] TRANSPEDICULAR SCREW SYSTEM AND METHOD OF USE

[75] Inventors: Rolando M. Puno, Prospect, Ky.; Philip A. Mellinger, Worthington, Ohio

[73] Assignee: Cross Medical Products, Columbus, Ohio

[21] Appl. No.: 946,319

[22] PCT Filed: Apr. 26, 1990

[86] PCT No.: PCT/US90/02286

§ 371 Date: Nov. 20, 1992

§ 102(e) Date: Nov. 20, 1992

[87] PCT Pub. No.: WO91/16020

PCT Pub. Date: Oct. 31, 1991

[51] Int. Cl.⁵ .............................................. A61F 5/00
[52] U.S. Cl. .................................... 606/72; 606/73; 606/61; 623/17
[58] Field of Search ............... 606/60, 61, 72, 73; 623/17

[56] References Cited

U.S. PATENT DOCUMENTS

| | | | |
|---|---|---|---|
| 4,179,905 | 1/1988 | Steffee | 128/69 |
| 4,611,580 | 9/1986 | Wu | 128/69 |
| 4,653,481 | 3/1987 | Howland et al. | 128/69 |
| 4,658,809 | 4/1987 | Ulrich et al. | 128/92 YM |
| 4,763,644 | 8/1988 | Webb | 128/69 |
| 4,805,602 | 2/1989 | Puno et al. | 606/73 |
| 4,913,134 | 4/1990 | Luque | 128/69 |
| 5,084,049 | 1/1992 | Asher et al. | 606/60 |
| 5,127,912 | 7/1992 | Ray et al. | 623/17 |
| 5,176,680 | 1/1993 | Vignaud et al. | 606/73 |

Primary Examiner—Stephen C. Pellegrino
Assistant Examiner—Sonya Harris
Attorney, Agent, or Firm—Hudak & Shunk Co.

[57] ABSTRACT

An apparatus is provided for the internal fixation of the spine. The apparatus comprises two sets of implants (8) each consisting of a rod (18) and a plurality of vertebral anchors (16). The rod (18) is secured to the vertebral elements by the vertebral anchors (16). The anchor (16) includes a transpedicular screw (21) which is secured to a vertebrae. The anchor (16) further includes an anchor seat (23) which captures the screw (21) and permits micromotion between the anchor seat (23) and screw (21). This seat (23) has a rod-receiving channel (51,52) which captures the rod (18). A cap (25) cooperates with the seat (23) to secure the rod (18) in the anchor (16). A nut (27) screws down from the top of the assembly onto the seat (23) to cause rod (18) receiving flanges (46,47) in the cap (23) to apply a compressive force to the rod (18). A method of therapy is presented in which the present implants (8) are inserted surgically into a patient.

3 Claims, 7 Drawing Sheets

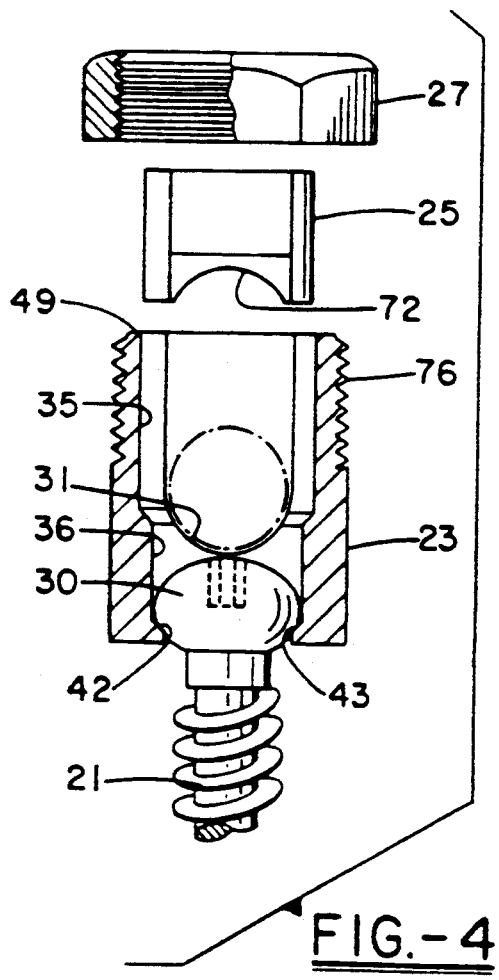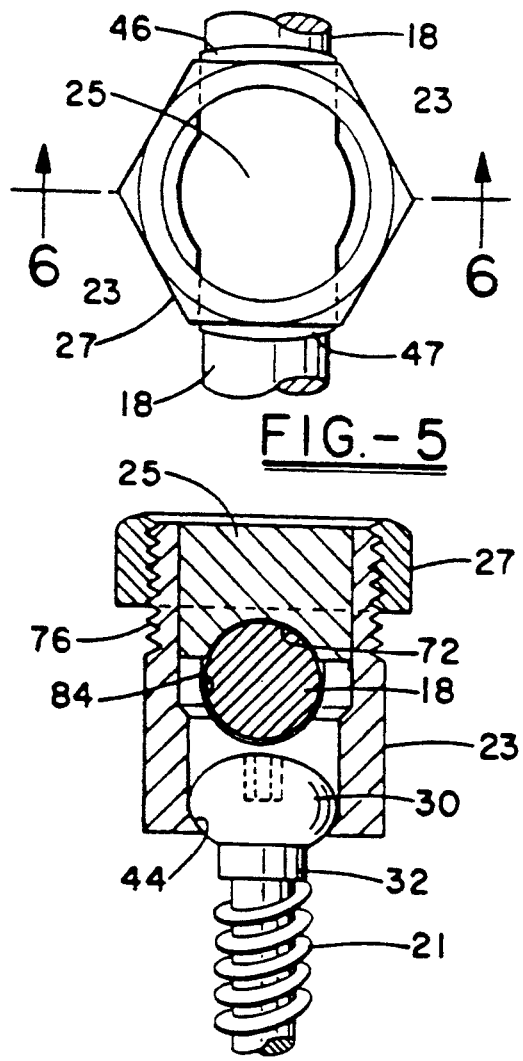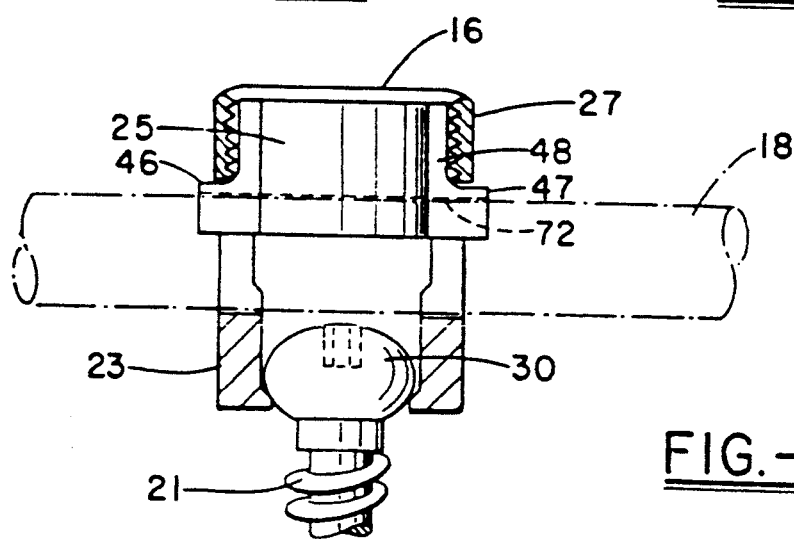

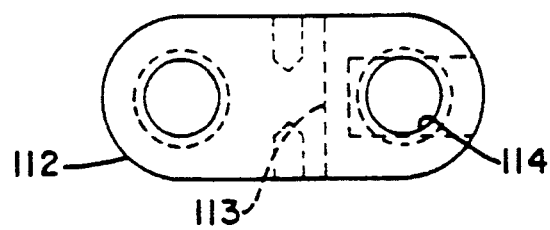
FIG.-8
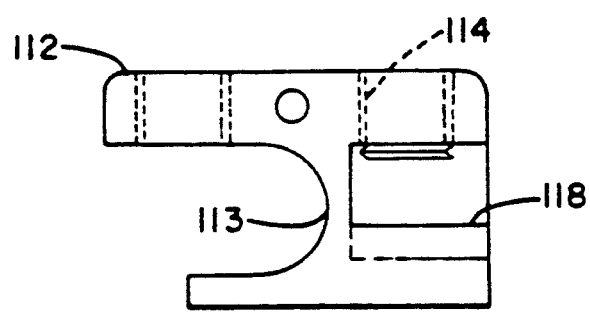
FIG.-9
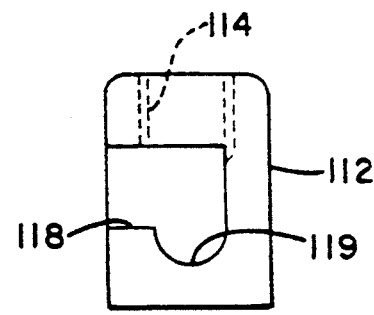
FIG.-10
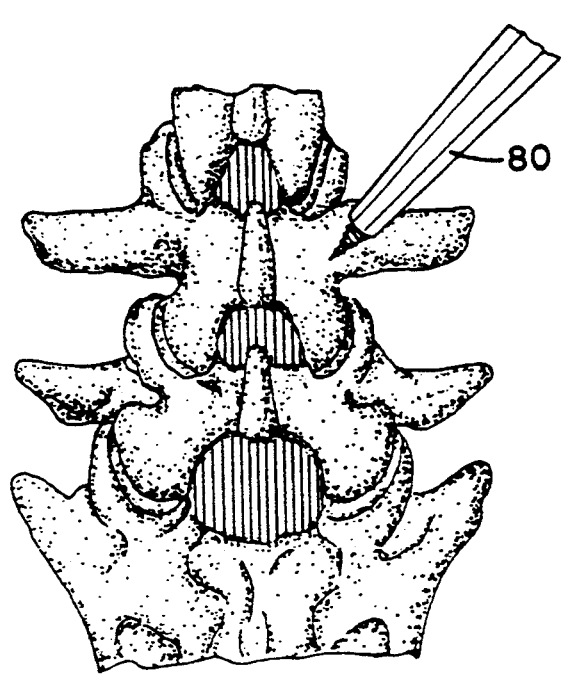
FIG.-11
FIG.-12

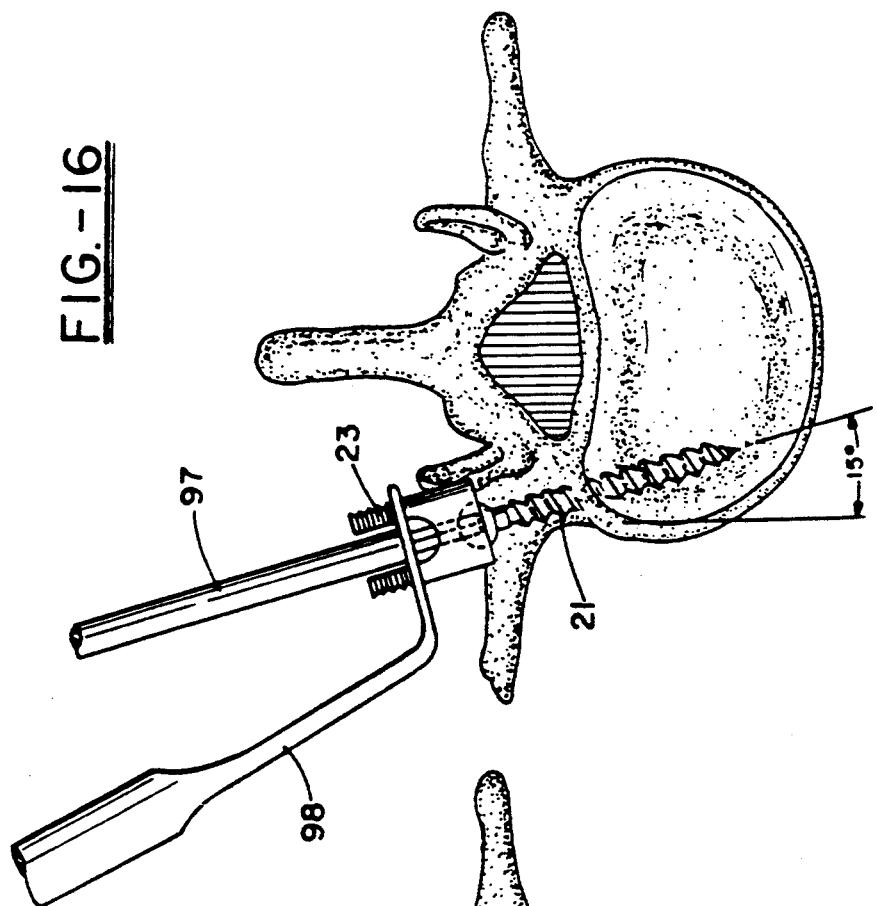
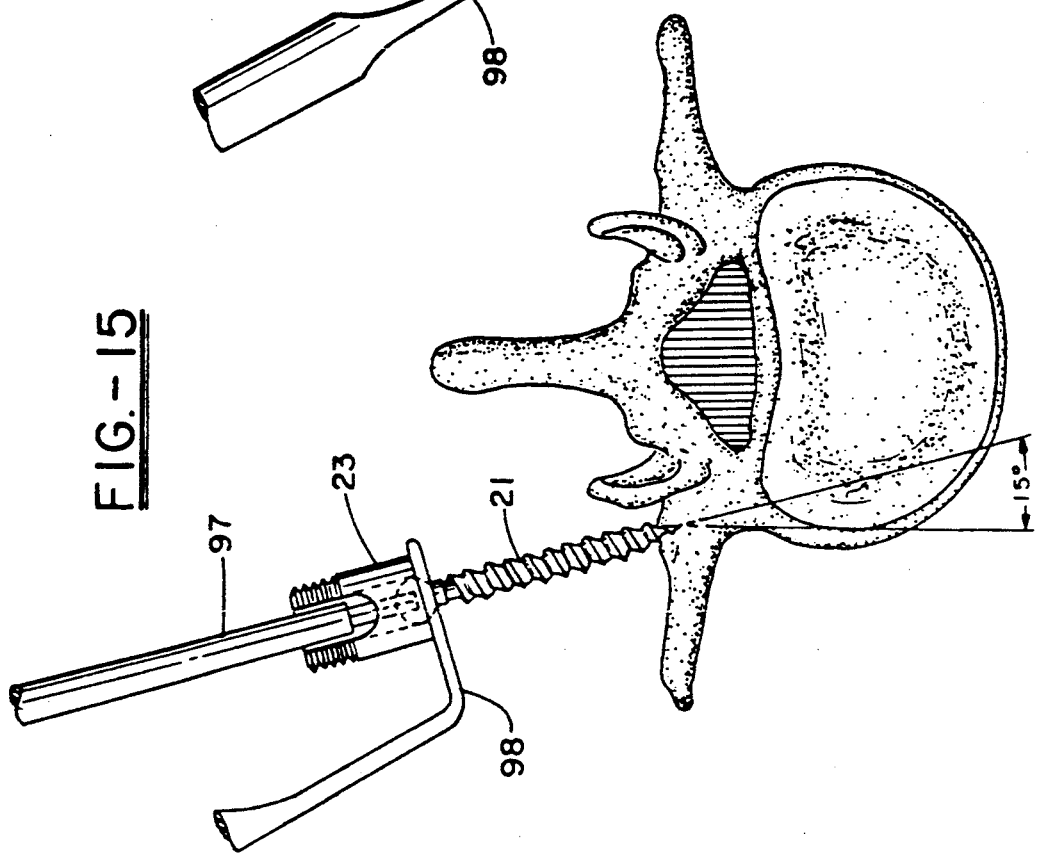

TRANSPEDICULAR SCREW SYSTEM AND METHOD OF USE

This invention relates generally to an apparatus for immobilization of the spine, and more particularly, to an apparatus for posterior internal fixation of the spine as well as to a method of therapy which utilizes the device.

Various methods of spinal immobilization have been known and used during this century in the treatment of spinal instability and displacement. The preferred treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form. Early in the century, post operative external immobilization such as the use of splints and casts was the favored method of treatment, however, as surgical techniques have become more sophisticated, various methods of internal and external fixation have been developed.

Internal fixation refers to therapeutic methods of stabilization which are wholly internal to the patient and include commonly known devices such as bone plates and pins. External fixation in contrast involves at least some portion of the stabilization device which is external to the patient's body. Internal fixation is now the favored method of immobilization since the patient is allowed greater freedom with the elimination of the external portion of the device and the possibility of infections, such as pin tract infection, is reduced.

Some of the indications treated by internal fixation of the spine include vertebral displacement and management such as kyphosis, spondylolisthesis and rotation; segmental instability, such as disc degeneration and fracture caused by disease and trauma and congenital defects; and tumor diseases.

A common problem with spinal fixation is the question of how to secure the fixation device to the spine without damaging the spinal cord. The pedicles are a favored area of attachment since they offer an area that is strong enough to hold the fixation device even when the patient suffers from osteoporosis. Since the middle 1950's, methods of fixation have utilized the pedicles. In early methods, screws extended through the facets into the pedicles. More recently, posterior methods of fixation have been developed which utilize wires that extend through the spinal canal and hold a rod against the lamina (such as the Luque system) or that utilize pedicular screws which extend into the pedicle and secure a plate which extends across several vertebral segments (such as the Steffee plate).

U.S. Pat. No. 4,805,602 to Puno, et al presents a system sharing advantage of both the wired implants and the plate. Specifically, that screw and rod system provides a rigidity which is intermediate between the wired implant and the plate systems and may be contoured to any plane.

The present invention represents an improvement in the technology and in the therapy advanced in U.S. Pat. No. 4,805,602. in particular, this invention greatly reduces the time required to perform the spinal operation as compared to the prior invention. As an example of such a reduction, the time for inserting the anchors may be cut from hours to around an hour.

Such a time saving represents a significant reduction in the risk associated with a surgical procedure. Further, the new design may be easier to use as the chances of cross-threading the nut unto the anchor are reduced and the nut is more accessible for tightening. This is cf particular significance in the bloody environment which obscures the spinal surgeon's access to the fixation device. The present device achieves this accessibility and attendant time savings without sacrificing the mechanical benefits of the earlier design. In particular, the anchor is designed so that it is not overly obtrusive. More specifically, the nut is thin and further is chamfered to reduce bulk and yet includes a thread design to achieve sufficient compression on the rod. The anchor system presents a flush upper surface and the total system is elegant and effective. Each anchor seat is secured by a cancellous screw which cooperates through a sloped bore in the anchor seat so as to provide a limited ball and socket motion. The design of the present invention incorporates a method of therapy for treating a spinal indication utilizing this internal fixator.

In particular, the present invention is viewed as having an application in the stabilization of the thoracolumbar, lumbar, and sacral spine. There are problems of fixation unique to this area of the spine such as the fact that the lumbar spine is normally lordotic and this lordosis must be preserved. In addition, indicated spinal decompression often requires a destabilization of the spine posteriorly. This may result in instability unless fusion is done, and fusion will often fail to become solid unless effective internal fixation is used. Finally, the points of sacral fixation are the weakest point of fixation. These problems are addressed by the present invention.

Prior art devices for posterior spinal fixation are discussed above as including the Steffee plate and the Luque System. A complete discussion of various internal devices are included in L. Wiltse, "Internal Fixation of the Lumbar Spine," *Clinical Orthopaedics and Related Research*, February 1986, No. 203, pp. 2–219.- Known implant configurations include facet screws, double distraction systems, compression distraction systems, springs, spinous process plates, wired implants and transpedicular screw and plate systems.

Common distraction and compression systems utilize a threaded rod and hooks which engage selected transverse lamina of the vertebrae. Examples of such systems include the Harrington distraction system sold by Zimmer USA, Inc., the Keene system shown in U.S. Pat. No. 4,269,178 and the Lewis-Greenlaw System illustrated in U.S. Pat. No. 4,085,744. U.S. Pat. No. 3,648,691 to Lumb, et al shows the use of spinous process plates.

Wired implants are favored by some orthopedic surgeons because of the flexibility of the system. Dr. Eduardo Luque has developed a wired implant system where two L-shaped rods are secured along their long sides to the vertebral laminas by means of wires which pass through the vertebral foramina. The short legs of the rods extend across the vertebrae between the spinous process. A similar wired implant is shown in U.S. Pat. No. 4,604,995 to Stephens, et al.

Transpedicular screw and plate systems rely on a screw threaded into a reamed canal generally positioned perpendicular to the longitudinal axis of the spine and horizontal or parallel to the transverse plane of the vertebral body. The screws engage a plate which has been bent to conform to the normal curvature of the spine or to the points of desired reduction. One screw and plate system which has been used with significant success is the Steffee system. In this system, the screws are inserted first, the spine plates are then inserted over the pedicle screws and then posterior tapered nuts are screwed on. The screws are tightened bilaterally until the plate is locked between two nuts.

While the wired implants have the advantages of facilitating vertebral alignment, permitting variation of the device to allow for variations in individual spines, this method of fixation includes the increased risk of damage to the neural structures. This risk can be countered by the use of transpedicular screws and plates. The pedicle presents an area for fixation of sufficient size and depth, that under careful conditions, the risk of damage to the neural elements (i.e., spinal cord and or nerve roots) is reduced. On the other hand, the use of plates with the screws rigidly linked results in the direct transfer of loads at the bone-screw interface which is the weakest link in the fixation spine construction. This can result in breakage of the screw or failure of the bone-screw interface prior to achieving fusion. In addition, the current plate designs are bulky and leave little surface for bone grafting and they cannot be contoured to account for lateral curvature of the spine (i.e., scoliosis).

The present invention utilizes a rod and vertebral anchors which holds the rod in position. Each anchor is secured to the vertebrae by a transpedicular screw member.

The screw and rod system of the present invention combines favorable attributes discussed above of wire implants and of screw plate systems. In particular, the present invention has an object of providing a fixation system which adequately immobilizes the lumbosacral area, allows relatively simple and riskfree insertion and provides adequate area for bone grafting.

Thus, the present invention combines advantages of the known devices as it provides suitable immobilization, in particular of the lumbosacral region, it allows for adaptation to individual patient characteristics such as degree of sagittal and/or coronal plane curvature; it allows for safe and relatively riskfree insertion; and it permits sufficient area for bone grafting.

Further, the present invention presents an improvement over the previous rod and anchor system as it streamlines the surgical procedure and increases the ease of insertion while maintaining the favorable attributes of the other system. Specifically, one less part is required and less time is required in preparation of the bony surface to receive the implant.

In order to achieve these advantages, the present design utilizes two implant sets on either side of the spinous processes. Each implant set includes a 0.25 inch diameter stainless steel (316L) rod which spans the vertebrae to be immobilized. Generally, an implant set is used on each side of the spinous process on the posterior side of the lamina and the transverse process. The rod is held in position by a stainless steel vertebral anchor which captures the rods. The anchor has a seat member which is secured to the vertebrae by a stainless steel transpedicular screw. The screw is separate from the anchor seat and thus provides for limited motion between the anchor seat and the vertebrae. In addition, this aspect of the design acts as a "shock-absorber" to prevent direct transfer of load from the rod to the bone-screw interface prior to achieving bony fusion, thereby decreasing the chance of failure of the screw or the bone-screw interface prior to achieving bony fusion. This greatly facilitates the surgical procedure and therapy incorporating this device.

In the preferred embodiment, the anchor comprises three members; an anchor seat having a bore which receives the screw and a rod-receiving channel transverse to the screw; a cap which mates with the anchor seat to capture the rod between the rod receiving channel and the cap; and an internally threaded collar or nut which engages external threads on the anchor seat to tighten the cap into position on the rod support as it is screwed downward into position on the anchor seat.

FIG. 4 is a cross-sectional of the anchor seat along line 4—4 with the rod shown in phantom;

FIG. 5 is a top plan view of the assembly;

FIG. 6 is a cross-section of the assembly shown in FIG. 4 taken along line 6—6;

FIG. 7 is a cross-section of the anchor seat and nut with the cap and screw and the rod shown in phantom;

FIG. 8 is a top view of the crosslink of the present invention;

FIG. 9 is a cross-section taken along line 9—9 of FIG. 8;

FIG. 10 is a cross-section taken along line 10—10 of FIG. 8;

FIG. 11 is a cross-section of the set screw;

FIG. 12 is a posterior view of the placement of the awl;

FIG. 15 is a cross-section of a vertebrae showing implantation of the anchor seat and transpedicular screw using a seat holder and hexagonal screw driver;

FIG. 16 is a cross-section of a vertebrae showing the transpedicular screw and the seat in position;

Figure 1:
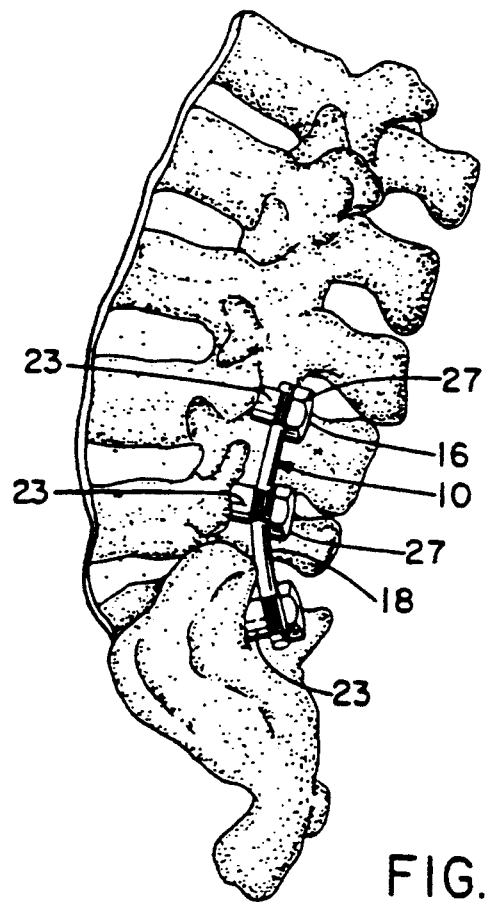
FIG. 1 is a side view of a spine with the invention in place.
Figure 2:
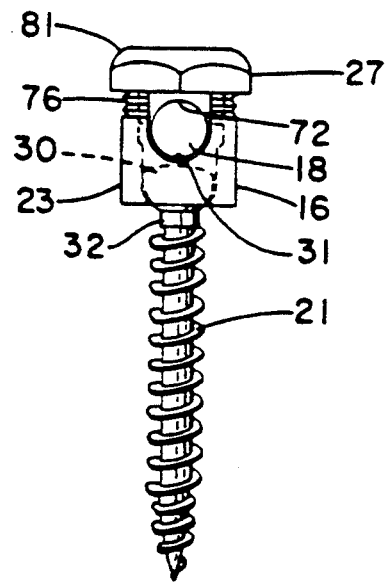
FIG. 2 is a side plan view of the vertebral anchor and rod of the present invention.
Figure 3:
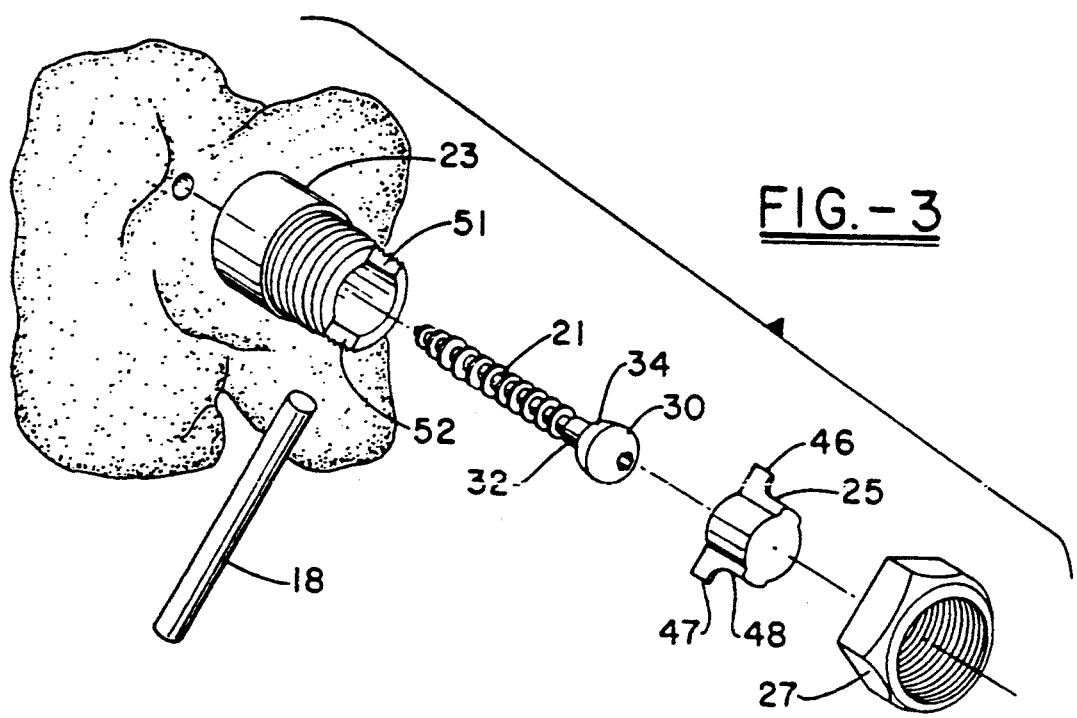
FIG. 3 is a posterior view of a vertebral body with an exploded view of the fixation device of the invention.
Figure 14:
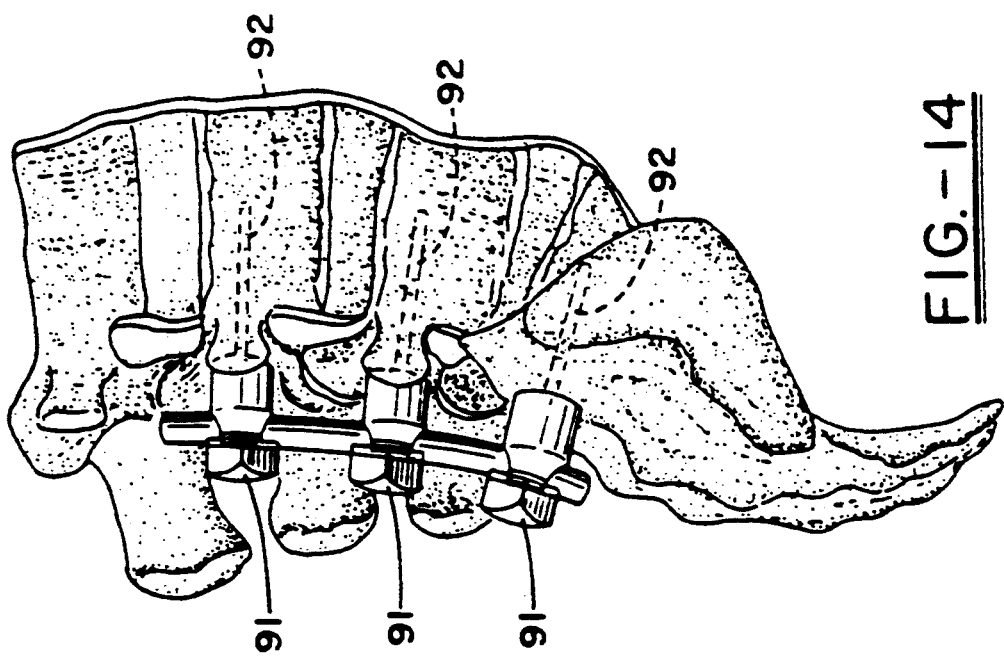
FIG. 14 is a side view showing the placement of the trial seats.
Figure 13:
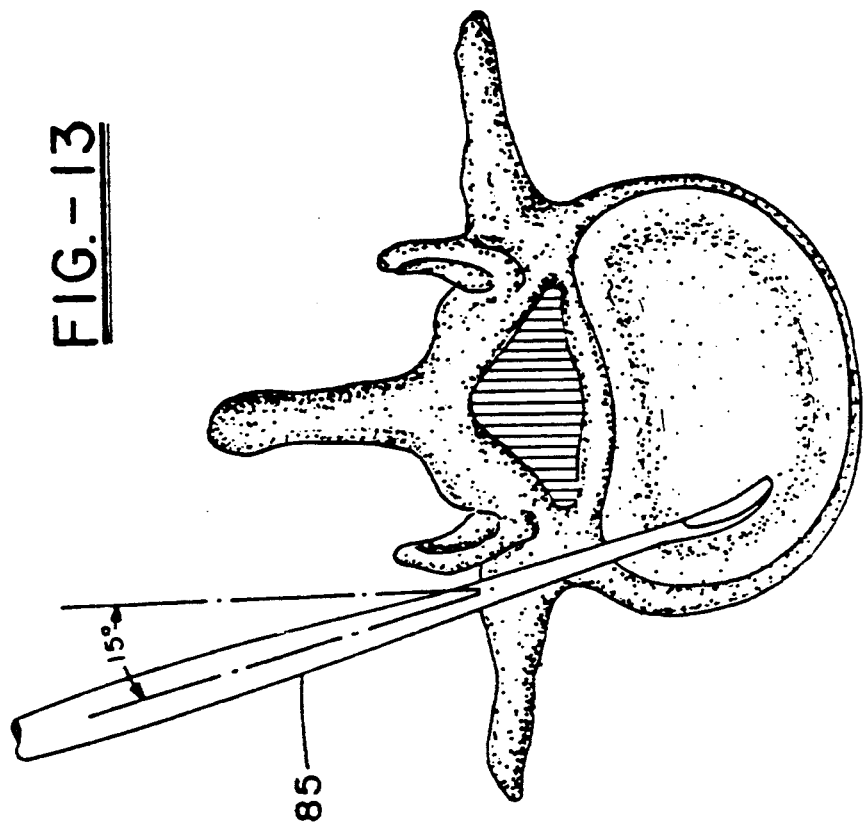
FIG. 13 is a cross-section of a vertebrae showing placement of the pedicle probe.
Figure 18:
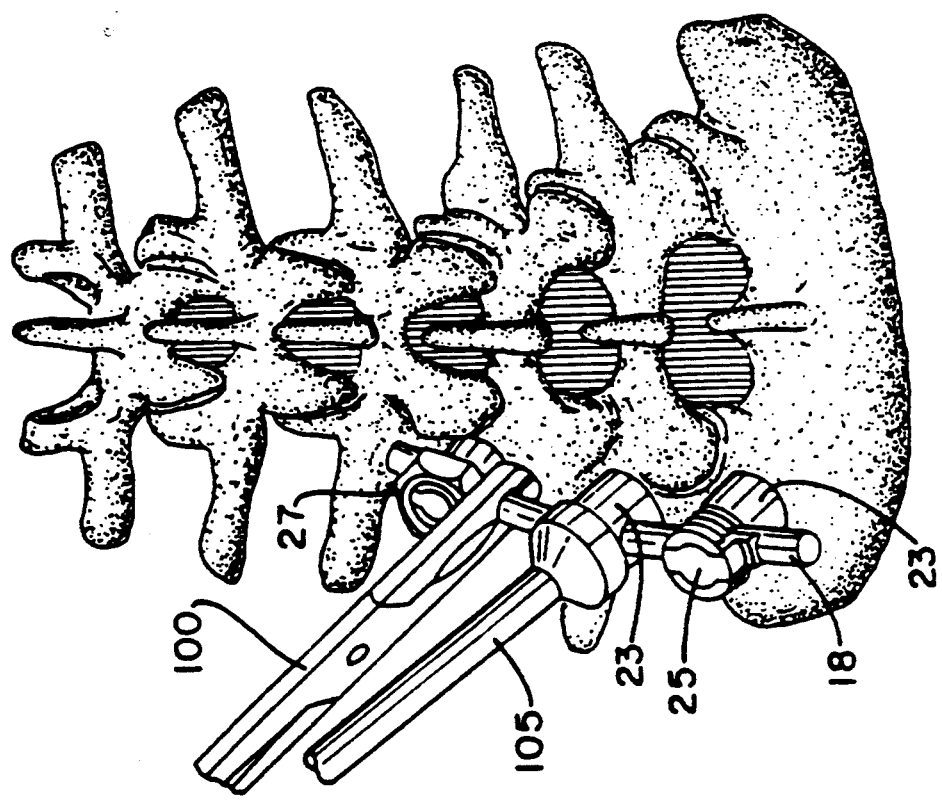
FIG. 18 is a posterior view showing tightening of the nuts on the anchor seats.
Figure 17:
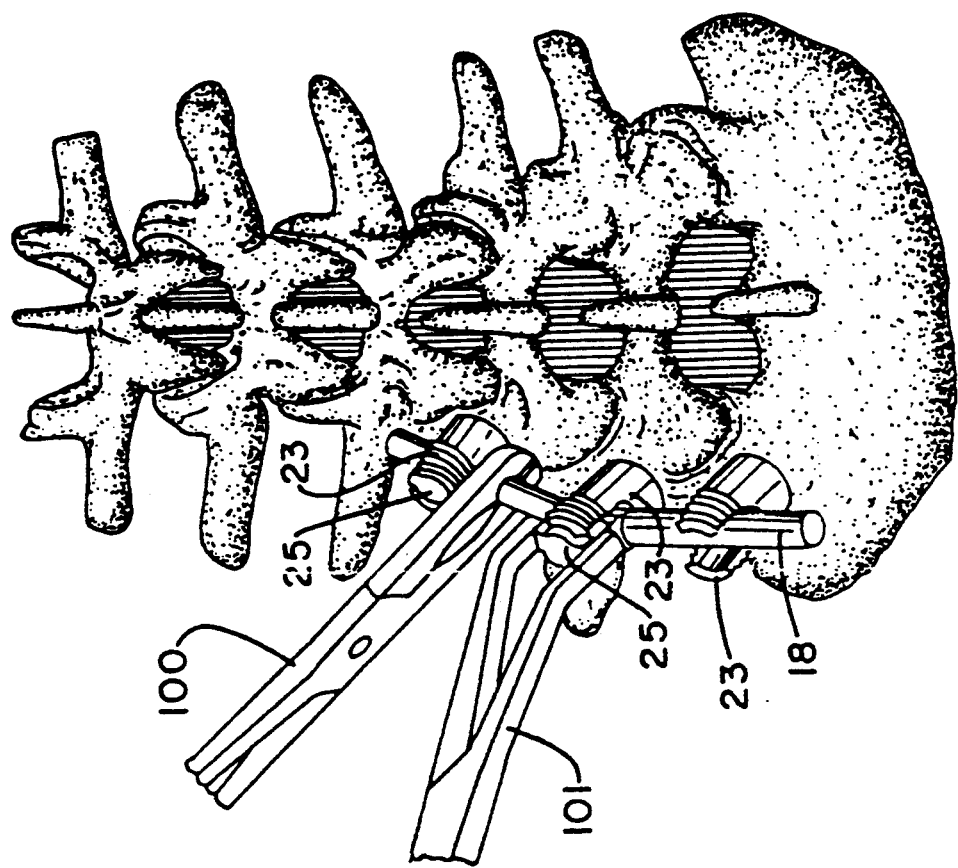
FIG. 17 is a posterior view showing installation of the rod and cap using the rod holder and cap holder.
Figure 20:
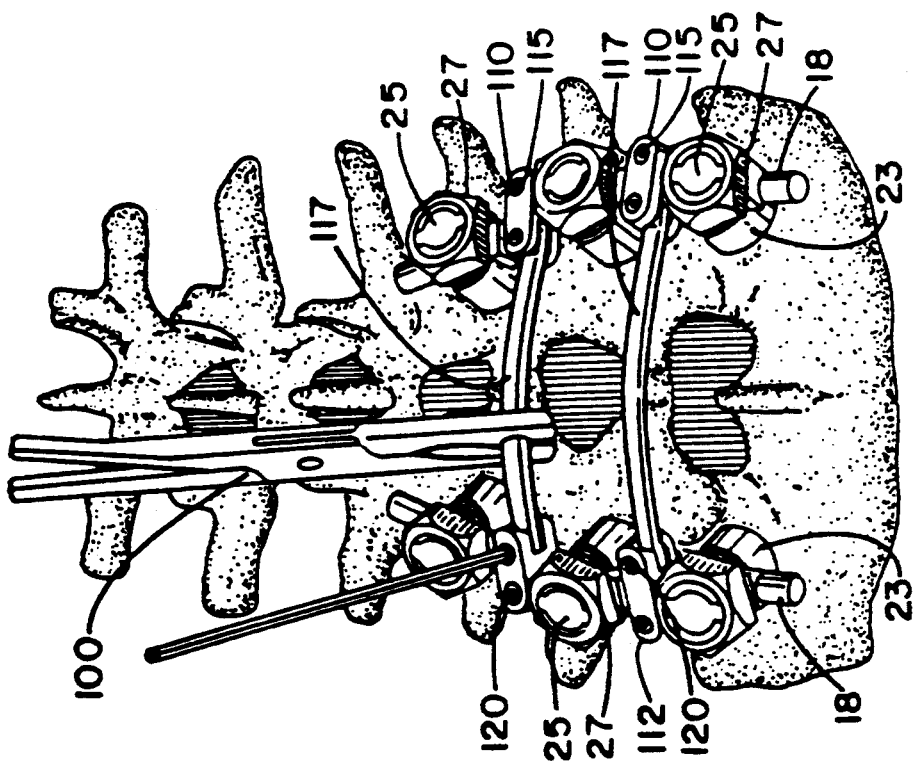
FIG. 20 is a posterior view showing positioning of the joining link between the crosslink and tightening of the set screw in the crosslink.
Figure 19:
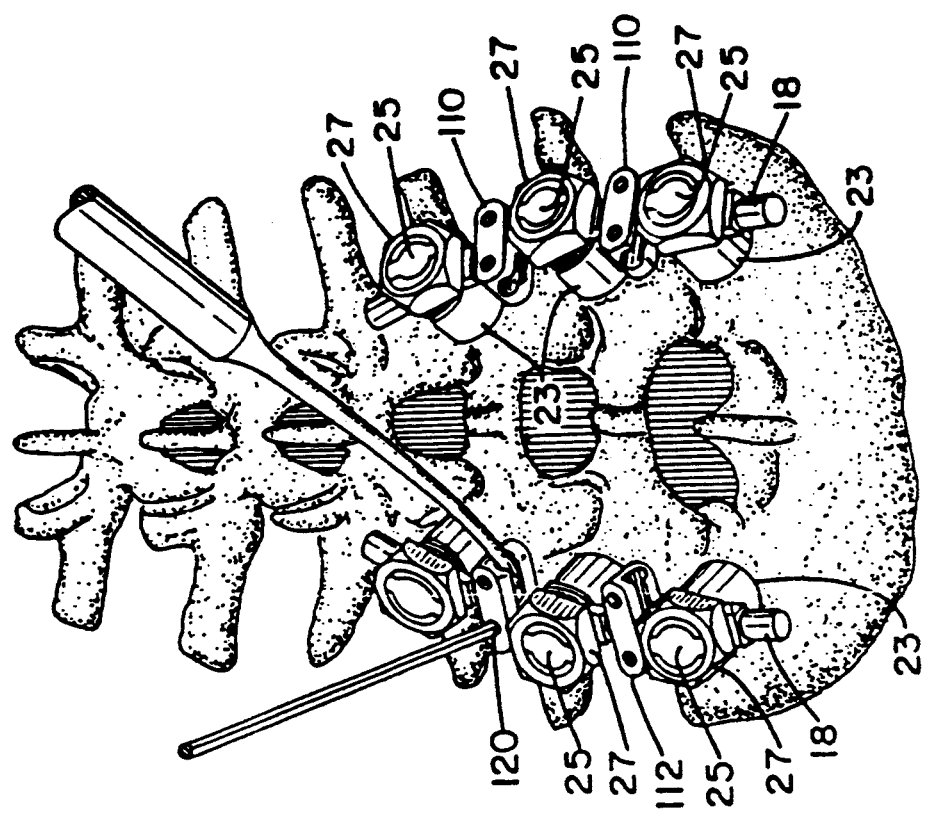
FIG. 19 is a posterior view showing installation of the crosslinks.

The anchor screw and rod system 10 of the present invention includes two implant sets 8 on either side of the spinous processes. Each set is comprised of a plurality of vertebral anchors 16 and a rod 18 which is of sufficient length to span the length of spine to be immobilized.

Each anchor 16 is positioned on the dorsal side of the vertebra and in general, a separate anchor 16 is used for each vertebrae comprising the length of spine to be stabilized. The rod 18 is held by the anchors 16 posterior to the vertebra.

The rod 18 is generally made of quarter inch stainless-steel rod (316L), but could be made of any material which has suitable biocompatibility and material strength characteristics. The rod should be able to withstand lateral bending forces and torsion since the system may be used to correct spinal displacement and curvature. On the other hand, it is important that the rod 18 can be bent to a certain extent so that the rod can be bent to the proper curvature for the individual application.

The vertebral anchor 16 comprises a transpedicular screw 21, an anchor seat 23, a cap 25, and a nut 27. The various anchor parts 16 can be made of any suitably strong biocompatible material such as stainless steel. The screw 21 which is shown is a standard stainless steel cancellous screw with 6.5 mm thread diameter. It is available in various lengths. The anchor 16 was designed for use with this screw since the screw is readily available, and it has a proven record in fracture fixation; and the size can be accommodated by the average adult pedicles of the lower thoracic, lumbar and the upper two sacral segments vertebrae.

The screw 21 includes a head 30 which accommodates a hex driver. The screw 21 includes a smooth shank 32 of 2–4 millimeters length which joins the rounded rear shoulder 34 of the head 30. After insertion, the screw 21 extends from the curve formed on the dorsal side of the posterior neural arch.

The anchor seat 23 is comprised of a hollow cup portion 49 which receives the screw and which includes opposing channels 51,52 to receive the rod 18. The cup 49 has a stepped central longitudinal opening 40 having an upper inner diameter section of about 0.358 and a smaller lower diameter section which slightly exceeds the diameter of the head 30 of the screw 21. This step eliminates unwanted motion between the screw 21 and the anchor 23. This lower diameter section is about 0.323 of an inch. The screw 21 passes through the two sections of the opening 40 within the rod support 25 until the rear shoulder 34 of the screw 21 encounters a detaining flange 42 within the central opening 40 of the rod support 23. The flange 42 has an internal surface at an angle of about 120 degrees and defines an opening 43 which has a diameter that exceeds the diameter of the shank 32 but which is smaller than that of the head 30 of the screw 31. The diameter of the opening at the flange is about 0.27 of an inch. The internal surface of the detaining flange 42 represents a sloped shoulder 44 which forms a socket for the rear shoulder 34 of the screw head 30. Thus, when the screw 21 engages the anchor seat 23, a limited ball-and-socket joint is formed which permits freedom of movement between the rod support 23 and the screw 21.

The anchor seat 23 has two opposing channel 51,52 of the proper diameter to cradle the rod 18. The channels 51,52 form a rod-receiving cradle which is about 0.37 of an inch long.

The height of the anchor seat 23 generally determines the amount that the anchor 26 project posterior of the vertebrae. This height ranges from 0.66 to 0.84 inches. However, if necessary, one or two washers may be added. These washers are smooth round washers having an outer diameter which corresponds to the diameter of the anchor seat, i.e., 0.5 inch, and height of 0.063 inch. The washer fits around the screw 21 and is positioned under the seat between the bone and the seat 23. The washers are useful in indication of where the patient is heavy or severely deformed.

On its external surface, the anchor seat 23 includes a threaded area 76. This area is 0.27 inch deep to the thread runout. A 45 degree chamfer is included at the top to facilitate threading the nut on the seat 23. The threads are at a count of 20 thread per inch. The nut 25 has a height of 0.19 inch and includes a chamfered area 81 on its top surface. This chamfered area 81 blunts the edges of the nut and eliminates sharp edges which could otherwise irritate the soft tissues post-operatively, two opposing clamping flanges 46,47 which each extend about 0.13 inch beyond a larger diameter area 46 of the cap 25. Two such larger diameter areas 48 exist and form opposing buttressing curves where the flanges 46,47 flow into the cup portion 59 of the cap 25. These two areas 48 mate with the channels 51,52 so that the seat 23 and the cap 25 complement each other to form a cylindrical unit into which the nut 27 is threaded. On its bottom, the cap 25 includes an arch 72 transverse to the longitudinal axis of the cap 25.

The nut 27 includes internal threads 83 which engage the external threaded area 76 on the anchor seat. The nut 27 is a hex nut which can be tightened relative to the seat 25.

As the nut 27 is rotated about the anchor seat 25, it cooperates with the top side of the flange 46,47 to tighten the clamp 25 in relation to the rod support 23. The rod 18 is gasped in the tunnel 84 formed between the rod-receiving channel 54 of the anchor seat 23 and the arch 72 of the cap 25.

As a further part of this invention, a cross-link 110 may be used to stabilize the rod members 18 against torsional rotation. The crosslink 110 may be used with this implant device or with any spinal implant which utilizes rods for longitudinal stability such as the Marrington rod system. It is preferable that two crosslinks are used to form a rectangular construct. Each crosslink 110 comprises two clamps 112, each secured to the main rods 18. Specifically, each clamp 112 includes a rod receiving channel 113 which accommodates the rod 18 and is locked into position relative thereto by a first set screw received in bore 114. The clamp further includes a link opening 118 which has a well 119 to accommodate a link 117 axially transverse to the main rod 18. This link 117 may be, for example a 4 mm Steinmann pin. The link 117 is locked into position by a second set screw which biases the link 117 into the well 119. The set screws 115 include a hexagonal opening 120 to receive a corresponding screwdriver. The screws 115 further include a terminal bevel at a 45 degree angle to facilitate locking the rod and link, respectively.

A method of therapy for use of the present device is described as follows:

Initially, the area of implantation is surgically approached. A longitudinal posterior midline incision is made over the spine. The incision is carried through the subcutaneous tissue and the fascia to the tips of the spinous processes. Subperiosteal dissection is performed over the laminas and transverse processes. The facet capsule and articular cartilage are removed in preparation for fusion.

The pedicle is located using an awl 80. The awl 80 is used to make a hole 4 mm deep at the intersection of a line drawn transversely through the midportion of the transverse process and a line drawn longitudinally through the lateral margin of superior articular facet.

A pedicle hole is made using a pedicle probe 85. The pedicle probe is inserted into the hole initially created by the awl 80 and rotated back and forth in a 90 degree arc of motion with a very gentle downward pressure. The surgeon feels a relatively soft gritty sensation of the cancellous bone within the pedicle and vertebral body during this procedure. The shaft of the probe 85 should end up at an angle of 10 to 15 degrees from the midline of the spine when used in the lumbar region. Great care should be taken not to penetrate the anterior cortex of the vertebral body with the probe 85.

The depth of the hole is determined by using the graduated markings on the pedicle probe 85. The appropriate size screw is then chosen for that particular pedicle. The same technique is repeated for the remaining pedicles that need to be instrumented. Roentgenographic assistance using plain radiographs or fluoroscopy may be recommended for proper insertion of the pedicle probe 85 and screw into the pedicle. Both anterior-posterior and lateral views are taken with metal markers in the holes of the pedicles to assure proper hole direction prior to insertion of the screws.

After the hole has been created, one of four sizes of anchor seats is then selected depending on the height needed for the rod to rest above the fusion bed. Trial anchors 91 may be inserted on rods 92. Washers are provided if additional height is needed.

The surgeon sequentially inserts an appropriate transpedicular screw 21 and anchor 23 seat assembly into each pedicle being instrumented. This is accomplished by using a hexagonal screwdriver 97. At the same time, the seat holder 98 grips the seat, thereby preventing rotation when the screw 21 is finally tightened.

After all the screws and anchor seats are in place, an appropriate length of 6.35 mm rod is chosen and contoured with a French bender to fit the seats. The rod 18 is placed using a rod holder 100 and secured on the seats with caps which are placed over the rod using a rod holder 101 and nuts which are tightened down over the cap with the use of a T-wrench 105.

The procedure is repeated on the other side of the spine over the same number of vertebral levels.

Finally, the crosslinks 110 may be applied for added torsional stability. The crosslink is composed of two clamps 112, each of which is secured to one of the two main rods with set screws 115. The clamps are then bridged together by a 4 mm Steinmann pin which acts as a crosslink 117 which is cut to the length equivalent to the distance between the clamps. The Steinmann pin is secured to the clamp 117 with a second set screw. It is recommended that at least two sets of crosslinks are used to provide a more stable construct.

In the case of arthrodesis, the fusion portion of the procedure is carried out in standard fashion. However, it is recommended to place some of the bone grafts in the lateral gutter after making the pedicle hole prior to screw insertion. The presence of the instrumentation can block the visualization of the fusion bed necessary for the proper placement of the graft. The remainder of the bone grafts are placed on the fusion bed after the instrumentation is completed.

While in accordance with the Patent Statutes, the best mode and preferred embodiment has been set forth, the scope of the invention is not limited thereto, but rather by the scope of the attached claims.

We claim:

1. A device for the stabilization of one or more bone segments, comprising:

at least two anchors and a rod, said anchors each comprising a screw, an anchor seat, a cap, and a nut, said screw having a shank joined to a head, said head having a rounded profile where it joins said shank; said anchor seat having an internal bore, said screw projecting through said bore to be received by said bone segment and said bore including a shoulder which cooperates with the rounded profile of the screw head and said anchor seat further including external threads and a channel to receive said rod; said cap having a smaller outer diameter portion which is received within said anchor seat bore and a large outer diameter portion forming at one end an arch including opposing rod holding flanges; said larger outer diameter portion mating with said rod receiving channel whereby said rod is captured between said arch and said channel; and said nut including top and bottom surfaces and having threads which mate with the threads of the anchor seat and said nut being posterior to said rod and tightening down toward rod whereby said bottom surface engages said opposing rod holding flanges and causes said cap to apply a compressive force to said rod.

2. A device as set forth in claim 1, wherein said device comprises two sets of implants, each of said implant sets comprising a rod and at least two of said anchors.

3. A device as set forth in claim 2 wherein said device further comprises two crosslinks, each of which links the rod of one implant set to the rod of the other implant set.

* * * * *